United States Patent [19]

Schäfer et al.

[11] Patent Number: 5,177,220
[45] Date of Patent: Jan. 5, 1993

[54] METHOD FOR THE ASYMMETRIC HYDROGENATION OF α-KETOCARBONYL COMPOUNDS TO OPTICALLY ACTIVE α-HYDROXYCARBONYL COMPOUNDS

[75] Inventors: Adolf Schäfer, Frankfurt; Dietrich Arntz, Oberursel, both of Fed. Rep. of Germany

[73] Assignee: Degussa Aktiengesellschaft, Fed. Rep. of Germany

[21] Appl. No.: 639,087

[22] Filed: Jan. 9, 1991

[30] Foreign Application Priority Data

Jan. 16, 1990 [DE] Fed. Rep. of Germany ....... 4001019

[51] Int. Cl.⁵ .......................................... C07D 307/26
[52] U.S. Cl. ..................................... 549/314; 560/179
[58] Field of Search ................. 549/319, 314; 560/179

[56] References Cited

U.S. PATENT DOCUMENTS

| 4,343,741 | 8/1982 | Townsend et al. | 548/412 |
| 4,634,775 | 1/1987 | Beck et al. | 548/402 |
| 4,652,657 | 3/1987 | Broger et al. | 548/402 |
| 4,668,795 | 5/1987 | Andrade et al. | 548/402 |

FOREIGN PATENT DOCUMENTS

| 0218970 | 9/1986 | European Pat. Off. |
| 0251164 | 6/1987 | European Pat. Off. |
| 0301457 | 7/1988 | European Pat. Off. |

Primary Examiner—Alan L. Rotman
Assistant Examiner—A. A. Owens
Attorney, Agent, or Firm—Cushman, Darby & Cushman

[57] ABSTRACT

Asymmetric hydrogenation of α-ketocarbonyl compounds, especially α-ketolactones, to the corresponding, optically active α-hydroxycarbonyl compounds in the presence of iridium diphosphine complexes as catalyst and dicarboxylic acid imides as co-catalyst.

20 Claims, No Drawings

METHOD FOR THE ASYMMETRIC HYDROGENATION OF α-KETOCARBONYL COMPOUNDS TO OPTICALLY ACTIVE α-HYDROXYCARBONYL COMPOUNDS

The present invention relates to a method for the asymmetric hydrogenation of α-ketocarbonyl compounds. The compounds used in the process include α-ketocarboxylic acids, α-ketocarboxylic acid esters, α-ketocarboxylic acid amides and especially α-ketolactones. The process converts the α-ketocarbonyl compounds to the corresponding optically active α-hydroxycarbonyl compounds. The process is carried out in the presence of chiral iridium complexes, which contain an optically active 1,2-diphosphine ligand, as catalyst and a cyclic dicarboxylic acid imide co-catalyst. The invention is particularly concerned with the preparation of (R)-(−)-pantolactone ((R)-(−)-3,3-dimethyl-2-hydroxy-γ-butyrolactone) from ketopantolactone (dihydro-4,4-dimethyl-2,3-furandione) by means of asymmetric hydrogenation.

BACKGROUND OF THE INVENTION

The preparation of optically active α-hydroxycarbonyl compounds from the corresponding α-ketocarbonyl compounds by means of asymmetric hydrogenation using chiral platinum-metal diphosphine complexes, especially rhodium (I)-1,4-diphosphine complexes, has been extensively investigated. Thus, British Patent 1,592,536 teaches the asymmetric hydrogenation of α-ketocarbonyl compounds such as e.g. pyruvic acid alkyl ester, phenyl- and alkylglyoxyl acid alkyl ester and ketopantolactone in the presence of rhodium complexes with an optically active 1,4-diphosphine ligand based on a 4-diarylphosphino-2-diarylphosphinomethylpyrrolidine or a 4,5-bis(diarylphosphinomethyl)-1,3-dioxolane which can also be substituted in the 2-position. Other publications such as e.g. published European Patent Applications EP-A 0 158 875, EP-A 0 218 970 and EP-A 0 251 164; Published German Patent Application DE-OS 33 02 697 U.S. Pat. No. 4 343 741; Chemistry Letters (The Chem. Soc. of Japan), (1978) pp. 297–298, (1984) pp. 1603–1606 and (1986) pp. 2061–2064 and Tetrahedron Letters 28 (1987) pp. 3675–3678 concern the further refinement of the above-mentioned method and the production of chiral 1,4-diphosphines as well as of rhodium complexes of the latter. I. OJIMA reports in J. Organomet. Chem. 195 (1985) pp. 239–248 on the mechanism of asymmetric induction by means of cationic Rh-(I) complexes and anionic Rh-(I) complexes formed in situ. In addition to the chiral diphosphine, the complexes contained diolefins and/or the solvent as supporting ligand as well as a coordinating or non-coordinating anion.

The previously known method using rhodium complexes with a chiral 1,4-diphosphane ligand permits the production of α-hydroxycarbonyl compounds, especially (R)-(−)-pantolactone, in a high yield and in relatively high optical yield; however, the optically active 1,4-diphosphines which have an especially good action and which are based on pyrrolidine can be produced only in multi-stage syntheses—cf. e.g. published European Patent Application EP-A 0 251 164—which makes the method expensive.

Published European Patent Applications EP-A 0 151 282 and EP-A 0 185 882 teach optically active 3,4-bis(diphenylphosphino) pyrrolidines as readily available 1,2-diphosphines for chiral rhodium complexes for asymmetric hydrogenation. These complexes were suggested as catalysts for the asymmetric hydrogenation of α-acylaminoacrylic acids. However, when using these and other chiral 1,2-diphosphines as ligands in rhodium complexes with diene supporting ligands for the asymmetric hydrogenation of ketopantolactone, it was only possible to obtain (R)-(−)-pantolactone in a low enantiomeric excess; in addition, the conversions were low—cf. reference Example 1. The use of chiral 1,2-diphosphines in complexes containing iridium as central atom instead of rhodium also resulted in the hydrogenation of ketopantolactone in only unsatisfactory conversions and enantiomeric excesses—cf. reference Example 2.

An iridium complex, namely, Ir(DIOP) (COD) Cl (COD=1,5-cyclooctadiene; DIOP=((−)-4,5-bis(diphenylphosphine)-2,2-dimethyl-1, 3-dioxolane) was also included in the investigations of I. OJIMA (cf. supra) on the mechanism of the asymmetric hydrogenation of α-ketocarbonyl compounds—cf. S. Brunie, J. Mazan, N. Langlois and H. B. Kagan, J. Organomet. Chem. 114, p. 225 (1976). According to the authors it was assumed from the conformation of the Ir complex that it was not likely to be asymmetrically inducing. A moderate optical induction and low conversions were observed by the applicant with the specified complex.

SUMMARY OF THE INVENTION

The object of the present invention is to provide a method for the asymmetric hydrogenation of α-ketocarbonyl compounds selected from the group consisting of α-ketocarboxylic acids, α-ketocarboxylic acid esters, α-ketocarboxylic acid amides and especially α-ketolactones to the corresponding optically active α-hydroxycarbonyl compounds in the presence of chiral platinum-metal diphosphine complexes as catalyst which permits optically active 1,2-diphosphines to be used as chiral ligands. The invention is particularly concerned with obtaining the α-hydroxycarbonyl compounds, especially (R)-(−)-pantolactone, in high yield and in high enantiomeric excess also using 1,2-diphosphines which can be obtained in an especially simple manner. A further object of the invention is to carry out the hydrogenation at high pressure without loss of enantioselectivity and catalytic activity.

These and other objects are achieved by using chiral iridium complexes which contain an optically active 1,2-diphosphine ligand of the general Formula Ia, Ib or Ic,

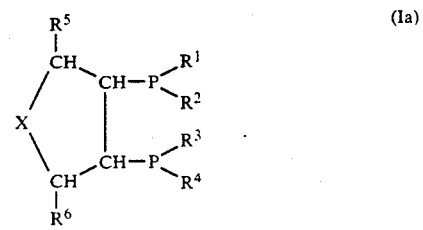

-continued

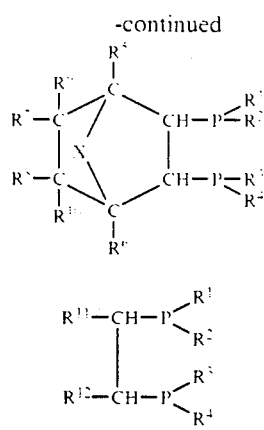

(Ib)

(Ic)

in which $R^1$, $R^2$, $R^3$ and $R^4$ are the same or different and signify $C_1$ to $C_8$ alkyl, which can be linear or branched, a cyclohexylmethyl, $C_5$ to $C_7$ cycloalkyl (which can exhibit one or two $C_1$ to $C_4$ alkyl substituents), benzyl or phenyl (the aromatic ring of which can contain $C_1$ to $C_4$ alkyl-, $C_1$ to $C_4$ alkoxy-, di-($C_1$ to $C_4$) alkylamino- or $C_1$ to $C_4$ alkyloxycarbonyl substituents) or $R^1R^2$ and/or $R^3R^4$ may represent an ortho-biphenylene group.

X stands for oxygen, the group $NR^{13}$, $CR^{14}R^{15}$, $-CR^{14}=CR^{15}-$ or $-CHR^{14}-CHR^{15}-$, in which $R^{13}$ signifies hydrogen, $C_1$ to $C_6$ alkyl, $C_5$ to $C_7$ cycloalkyl, benzyl or an acyl group from the series -COalkyl, -COaryl, -COOalkyl, -COOaryl, -SO$_2$aryl, -P(O)aryl$_2$, in which the alkyl group contains 1 to 4 carbon atoms and aryl stands for phenyl or naphthyl and can contain one or two $C_1$ to $C_4$ alkyl-, $C_1$ to $C_4$ alkoxy-, di-($C_1$ to $C_4$) alkylamino-, $C_1$ to $C_4$ alkoxycarbonyl substituents and $R^{14}$ and $R^{15}$ are the same or different and signify hydrogen, $C_1$ to $C_4$ alkyl or phenyl.

$R^5$ and $R^6$ are the same or different and signify hydrogen, $C_1$ to $C_4$ alkyl or phenyl.

$R^7$ and $R^8$ are the same or different and signify hydrogen, phenyl, $C_1$ to $C_4$ alkoxycarbonyl or $C_1$ to $C_4$ alkyl.

$R^{11}$ and $R^{12}$ are the same or different and signify $C_1$ to $C_6$ alkyl, benzyl or phenyl, or one of the groups $R^{11}$ and $R^{12}$ can also be hydrogen or, under the condition that at least one phosphorus atom or one of the groups $R^1$ to $R^4$ is chiral, $R^{11}$ and $R^{12}$ also stand for hydrogen.

The hydrogenation using these iridium complexes is carried out in the presence of a co-catalyst from the group of cyclic dicarboxylic acid imides of the general Formula II

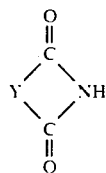

(II)

in which Y signifies an ethylene- or tri- or tetramethylene group, which can have a phenyl group or one or two $C_1$ to $C_8$ alkyl substituents. Y can also signify a vinylene- or ortho-arylene group, which can contain one or two substituents from the group ($C_1$ to $C_4$) alkyl, ($C_1$ to $C_4$) alkoxy, ($C_1$ to $C_4$) alkoxycarbonyl, di-($C_1$ to $C_4$) alkylamino.

The essence of the invention resides in the use of the combination of a chiral iridium-, or, less preferably, a rhodium, complex with an optically active 1,2-diphosphine ligand as catalyst with a cyclic dicarboxylic acid imide of the general Formula II, which combination is very effective both as regards hydrogenation activity and also asymmetric induction. As can be seen from reference Examples 1 and 2, both the conversion and also the enantiomeric excesses are far below the values desired for industrial purposes if the asymmetric hydrogenation of the α-ketocarbonyl compounds of the invention is carried out with the chiral Ir- and Rh complexes, but in the absence of the co-catalyst.

This action of the cyclic dicarboxylic acid imides use as co-catalyst could not have been foreseen. According to the method described in published European Patent Application EP-A 0 301 457, imines can be asymmetrically hydrated with chiral iridium (diene) - (1,2-diphosphine) complexes. According to the preferred embodiment, ammonium halides, especially iodides, which obviously provide a co-catalyzing action, are also used. The use of such substances at the same time provides essentially no increase of the optical yield in the asymmetric hydrogenation of α-ketocarbonyl compounds.

The co-catalysts of the present invention exert a vigorous co-catalyzing action both on cationic as well as neutral iridium complexes of the general structure $[Ir(1,2\text{-DP}) L_2]^+ A^-$ and $[Ir(1,2\text{-DP})(L)_2(Z)]$, in which 1,2-DP signifies an optically active 1,2-diphosphine, L a supporting ligand and Z a coordinating anion. Only the presence of the co-catalyst makes it possible to achieve high optical yields or at least to significantly increase the enantioselectivity. Surprisingly, the catalyst is activated at the same time by the co-catalyst, as a result of which the hydrogenation times are reduced and the conversions increased. A further advantage of the catalyst/co-catalyst combination of the invention resides in the fact that the catalyst is stabilized, that is, even under drastic conditions of hydrogenation such as in particular at pressures between 5 and 20 MPa, no cluster formation and associated inactivation of the catalyst or even precipitation of the iridium occurs.

The enantiomeric excess is also increased by using cyclic dicarboxylic acid imides in the asymmetric hydrogenation of α-ketocarbonyl compounds in the presence of rhodium complexes identical in structure to the above-mentioned Ir complexes —in the case of pantolactone from approximately 12% ee to values of 76% ee (ee signifies the excess of enantiomers); however, the optical yields fluctuate greatly without any reasons which could be explained by prior experience.

The catalysts are chiral iridium (I) complexes which are soluble in the usual solvents such as those frequently used for hydrogenation. However, the catalysts can also be bound to a carrier material, e.g. a cation exchanger or a polymer with coordinating carboxylate groups. Soluble complexes are preferred and are added to the hydrogenation batch or can be formed in situ from a catalyst precursor and an optically active diphosphine. In addition to the 1,2-diphosphine ligand (1,2-DP), the neutral Ir complexes also contain a Z anion and two L supporting ligands, each with one bonding position, or contain one supporting ligand with two bonding positions. The supporting ligands are substances with at least electron pair suitable for coordination purposes. The supporting ligands added with the catalyst or the preliminary catalytic form into the hydrogenation batch can be replaced entirely or partially by coordinating solvents such as e.g. alcohols, acetonitrile and, it is assumed, the co-catalyst. Among the possible supporting ligands, nitriles such as benzonitrile or lower alkylnitriles and olefins have achieved practical significance. Lower monoolefins and especially diolefins are especially preferred. The anion is preferably chloride, bromide and iodide. Coordinating carboxylates such as those known from Published European Patent Application EP-A 0 218 970 can also be used. Z equal to chloride is especially preferred because the catalysts can be readily prepared from Ir (III) chloride hydrate.

The cationic Ir (I) catalysts also contain a 1,2-diphosphine ligand (1,2-DP) and two L supporting ligands with the same significance as was the case with the previously characterized neutral complexes; the non-coordinated anion is preferably $BF_4^-$, $PF_6^-$, $ClO_4^-$ but also $(C_6H_5)_4B^-$, $CF_3SO_3^-$, $SbCl_6^-$, $SbF_6^-$. Especially preferred Ir (I) complexes are $[Ir(en)_2(1,2\text{-}DP)(Z)]$ (IIIa) and $[Ir(en)_2(1,2\text{-}DP)]^+A^-$ (IIIb) in which en, 1,2-DP, Z and A have the above-mentioned significance. Especially preferred complexes contain a diene as (en)$_2$, especially 1,5-cyclooctadiene (COD), 2,5-norbornadiene (NBD) as well as non-conjugated hexadiene.

The Ir (I) catalysts can be prepared in a known manner or in a manner analogous to rhodium complexes with the same structure. Reference is made Inorg. Chim. Acta 73 (1983) p. 275 ff; S. Brunie et al., J. Organomet. Chem. 114 (1976), pp. 225–235; M. Green et al., J. Chem. Soc. (A) (1971) p. 2334 ff.; EP-A 0 158 875, the disclosures of which are incorporated by reference. Complexes of the type $[Ir(en)_2Z]_2$, especially e.g. $[Ir(COD)Cl]_2$, have proven to be an especially suitable precursor for the preparation of the catalyst. The addition of the optically active diphosphine to said precursor yields neutral complexes of the type of general Formula IIIa. If an alkali or ammonium salt with a non-coordinating A anion is added after the diphosphine to a solution of $[Ir(en)_2Z]_2$, the cationic catalyst of the type of general Formula IIIb can be obtained.

The co-catalyst of general Formula II is constituted by cyclic dicarboxylic acid imides with 5 to 7 ring members. The ring can be saturated, as in the case of the quite particularly preferred succinimide. However, the ring can also contain a double bond, as in the case of maleinimide or phthalimide. The ring-forming members of group Y with 2 to 4 carbon atoms can be alkyl-substituted. Among the co-catalysts of the series of aryl-ortho-dicarboxylic acid imides, in which Y in Formula II signifies an ortho-arylene group which is optionally mono- or disubstituted, ortho-phthalimide, 1,2-, 2,3- or 1,8-naphthalene dicarboxylic acid imide are preferred.

The Ir catalyst and the co-catalyst are used in a molar ratio of 1:1 to 1:50, preferably 1:2 to 1:25 and especially 1:3 to 1:6 during the hydrogenation. The molar ratio of the Ir catalyst to the substrate to be hydrogenated is generally in a range of 1:100 to 1:10,000, preferably 1:200 to 1:2,000.

Most of the optically active 1,2-diphosphines of the general Formulas Ia, Ib and Ic to be used in the method of the invention are known. Representative examples of these families, in as far as they are not known already per se, can be prepared in a known manner. Reference is made to H. B. Kagan "Chiral Ligands for Asymmetric Catalysis" in Asymmetric Synthesis, Vol. 5 (1985), pp. 13–23; published European Patent Applications EP-A 0 151 282 and EP-A 0 185 882, the disclosures of which are incorporated herein by reference. The 1,2-diphosphines can exhibit one or more chirality centers. In principle, one or both phosphorus atoms can be chiral; preferably, one or two chirality centers are located in the molecule part which comprises the $PR^1R^2$- and $PR^3R^4$ groups in vicinal position. Such 1,2-diphosphines are preferred in which the groups $PR^1R^2$ and $PR^3R^4$ are identical and thus $R^1=R^3$ and $R^2=R^4$. 1,2-diphosphines with at least one, preferably two identical aryl groups per phosphorus atom, especially phenyl, are especially readily accessible, at the same time very effective and especially to be preferred.

Diphosphines of the general Formula Ia with $R^5=R^6$ and especially $R^5=R^6=H$ are preferred; this applies in particular to the compounds with $X=NR^{13}$ and two identical phosphino groups on the pyrrolidine ring. Optically active 3,4-bis(diarylphosphino) pyrrolidines can be obtained in a simple manner in a few steps from natural tartaric acid.

The diphosphines of general Formula Ib are bicyclic compounds like those which can be obtained e.g. by means of the Diels-Alder addition of a dienophile to a cyclic diene with previous or subsequent introduction of the phosphino groups—cf. H. B. Kagan, loc. cit. Compounds are preferred in which $R^5=R^6=R^7=R^8=$ hydrogen and $PR^1R^2=PR^3R^4$. The use of 2,3-bis(diphenylphosphino)-bicyclo-[2.2.1]-hept-5-ene is especially advantageous.

Diphosphines of the Ic type are preferred in which $PR^1R^2$ and $PR^3R^4$ are identical. $R^{11}$ signifies hydrogen or methyl and $R^{12}$ a linear or branched $C_1$ to $C_4$ alkyl group or a phenyl, benzyl or cyclohexyl group. Compounds in which $R^{11}$ is hydrogen can be obtained from natural α-amino acids or α-hydroxycarboxylic acids, in which case the α-acids are first converted into the α-hydroxycarboxylic acids and are then converted in a known manner into the optically active diphosphines—cf. H. B. Kagan, loc. cit.

The substrates to be asymmetrically hydrogenated, the α-ketocarbonyl compounds, can be esters, amides, carboxylic acids and especially α-ketolactones. In addition to the α-ketocarbonyl grouping, they can contain such functional groups or substituents which do not change under the selected conditions of hydrogenation. The preferred α-ketolactones constitute 5 to 7-member rings. These rings can comprise e.g. one or more lower alkyl groups with 1 to 6 carbon atoms or aryl groups which can optionally be substituted. An especially preferred substrate is α-ketopantolactone.

The lactone ring can also be connected via one or two carbon atoms to a further 5 to 7-member cycloaliphatic ring. Among the open-chain α-ketocarbonyl compounds, those with a linear or branched $C_1$ to $C_6$ alkyl-, $C_5$ or $C_6$ cycloalkyl- or phenyl group, which can also contain ($C_1$-$C_4$) alkyl-, ($C_1$-$C_4$) alkoxy, ($C_1$-$C_4$) alkoxy carbonyl, di-($C_1$-$C_4$) alkylamino, in addition to the keto group to be hydrogenated are preferred. The preferred substituents on the carbonyl group of open-chain α-ketocarbonyl compounds adjacent to the keto group are alkoxy groups with 1 to 12 carbon atoms which can be linear, branched or cyclic and even aryl-substituted; lower alkoxy groups with 1 to 4 carbon atoms are preferred.

The asymmetric hydrogenation is customarily carried out in the presence of an organic solvent for the α-ketocarbonyl compound and, when carrier-bound Ir catalysts are not used, for the catalyst and co-catalyst.

Solvents from the series of aromatic hydrocarbons, ethers, $C_1$ to $C_6$ alcohols, halogenated hydrocarbons, which are used alone or in the form of solvent mixtures, are especially suitable. The enantiomeric excess attainable in the asymmetric hydrogenation and also the conversion are very dependent on the solvent system, so that a preliminary test is desirable to determine whether a particular solvent is suitable. Mixtures consisting of an aromatic hydrocarbon and of a lower alcohol are especially advantageous, in particular e.g. mixtures of toluene or xylene with a $C_3$ to $C_5$ alcohol. As follows from the examples, a toluene/tert. butanol mixture in a volumetric ratio of approximately 1:3 is especially advantageous if α-ketopantolactone is to be hydrogenated to (R)-(−)-pantolactone.

The hydrogenation takes place at pressures in a range of 0.1 to 20 MPa, preferably at 0.5 to 12 MPa. The space-time yield is increased by raising the pressure.

The hydrogenation temperature is in general 10° to 100° C.; however, lower or higher temperatures are possible in principle. The hydrogenation is carried out with particular preference at 30° to 70° C.

The workup of the hydrogenated reaction mixture takes place in known manner. The enantiomeric excess (% ee) can be determined with advantage with gas chromatography on columns with a chiral phase such as e.g. chirasil or cyclodextrins after the α-hydroxycarbonyl compound is converted to an appropriate derivative.

As a result of the method of the invention, optically active 1,2-diphosphines which resulted previously only in unsatisfactory conversions and very low enantiomeric excesses can now be used as chiral ligands in platinum-metal complexes, especially iridium complexes. This has expanded the possibilities of asymmetrically hydrogenating α-ketocarbonyl compounds in the presence of chiral catalysts.

DETAILED DESCRIPTION OF PREFERRED EMBODIMENTS

The following examples further explain the invention. Abbreviations used in the following:

NBDPP = (3R,4R)-1-benzyl-3, 4-bis-(diphenylphosphino)pyrrolidine;
BDPPP = (3R,4R)-bis(diphenylphosphino)pyrrolidine;
COD = 1,5-cyclooctadiene;
NBD = norbornadiene;
Norphos = (2R,3R)-(−)-2,3-bis(diphenylphosphino)bicyclo-2.2.1-hept-5-ene
(S)/(K) = molar ratio of substrate to catalyst

EXAMPLE 1

(Reference Example)

The asymmetric hydrogenation of ketopantolactone (dihydro-4,4-dimethyl-2,3-furandione) with chiral rhodium-1,2-diphosphine complexes to optically active pantolactone.

The hydrogenation took place under the conditions indicated in the table. The catalyst was formed in situ from $[Rh(en)_2Cl]_2$ and the diphosphine.

See table 1.

The tests demonstrate that the conversion and the enantiomeric excesses are very low when the hydrogenation with Rh complexes takes place in the absence of the co-catalyst of the invention.

EXAMPLE 2

(Reference Example)

The asymmetric hydrogenation of ketopantolactone with chiral iridium-1,2-diphosphine complexes. Cationic Ir complexes were used which were preformed. The test conditions and results are described in the following table using the same abbreviations as in Example 1.

See table 2.

TABLE 1

| Catalyst/ solvent | (S)/(K) | Pressure MPa | Time (h) | Conversion (%) | Enantiomeric excess (% ee) | (Config.) |
|---|---|---|---|---|---|---|
| [Rh(C$_2$H$_4$)$_2$Cl]$_2$- NBDPP/Toluene | 205 | 5.3 | 24 | 4.1 | 12.4 | (R) |
| [Rh(COD)Cl]$_2$- NBDPP/Toluene | 217 | 5.0 | 24 | 18.3 | 17.8 | (R) |
| [Rh(C$_2$H$_4$)$_2$Cl]$_2$- BDPPP/Toluene | 202 | 5.0 | 24 | 5.6 | 3.0 | (R) |
| [Rh(NBD)Cl]$_2$- BDPPP/Toluene | 197 | 5.2 | 24 | 8.6 | 2.0 | (R) |
| [Rh(COD)Cl]$_2$- BDPPP/Toluene | 194 | 5.1 | 24 | 6.8 | 8.4 | (R) |
| [Rh(COD)Cl]$_2$- Norphos/Toluene | 202 | 5.1 | 24 | 6.8 | 10.8 | (S) |

TABLE 2

| Catalyst/ solvent | (S)/(K) | Pressure (MPa) | Temp. (°C.) | Time (h) | Conversion (%) | Enantiomeric excess (% ee (R)) |
|---|---|---|---|---|---|---|
| [Ir(COD)(NBDPP)]- BF$_4$/Toluene | 205 | 1.0 | 50 | 8-9 | 14.8 | 3.6-8.0 |
| [Ir(COD)(BDPPP)]- BF$_4$/Toluene | 200 | 1.0 | 50 | 10 | 12.3 | 3.0 |

(S)/(K) = Molar ratio substrate:catalyst

EXAMPLE 3 a) General Working Instructions For Hydrogenation With Isolated, Cationic and Neutral Complexes Initially, the catalyst and the co-catalyst are dissolved in 100 ml solvent in a Schlenk tube under argon. The clear catalytic solution is then added to a solution of the α-ketocarbonyl compound (40 mmoles), also prepared under argon, in 100 ml solvent. This mixture is then drawn by suction into an evacuated 500 ml autoclave. Hydrogen is now introduced until the desired pressure is achieved and the mixture is heated to the desired temperature. A constant pressure is maintained by a pressure-regulating device and the pressure drop is registered at the storage container. After the end of the absorption of $H_2$, the solvent is distilled off under reduced pressure from the reaction mixture in the usual manner. The residue is then subjected to a solid distillation in an oil-pump vacuum in order to separate the hydrogenated product from the catalyst. The product obtained is then characterized via $^1$H-NMR, gas chromatography and specific rotation.

b) General Working Instructions For Hydrogenation With In Situ Catalysts 40 mmoles of the α-ketocarbonyl compound are placed in a 500 ml 2-neck flask, the flask is evacuated and charged with argon. Then, 150 ml of the solvent or of the solvent mixture are added, followed by the co-catalyst. 0.1 mmole Ir(1,5-COD)Cl$_2$ and 0.204 mmole ligand are placed in a Schlenk tube under argon for a substrate/complex molar ratio of 200:1 and combined with 50 ml solvent or solvent mixture. The mixture is agitated approximately 30 minutes until a homogeneous yellow to orange solution has formed. After the complex solution has been combined with the substrate solution in a 500 ml autoclave, the mixture is hydrogenated as described in a) and worked up thereafter.

c) Preparation of Cationic Ir Complexes: [Ir(1.5 COD)((R.R)-NBDPP)]BF$_4$ 1.3 g [Ir(1,3-COD)Cl]$_2$ (1.94 mmoles) and 2.07 g (R.R)-1-benzyl-3,4-bis(diphenylphosphino) pyrrolidine (=505 NBDPP) (3.9 mmoles) are dissolved under argon at room temperature in 50 ml absolute methanol. The deep red solution which forms is agitated 0.5 h. A solution of 0.9 g NaBF$_4$ (8.2 mmoles) in 50 ml water (free of O$_2$) is subsequently added in drop-by-drop over a period of 1.5 h. A reddish-violet precipitate is formed. The resulting suspension is agitated 1 h further and then filtered on a frit. It is washed once with 20 ml water (free of O$_2$) and 3 times with 5 ml absolute ether per time. After drying in a vacuum, the product is recrystallized from 10 ml absolute methylene chloride and 20 ml absolute ether to provide 3.3 g reddish violet crystals (92.4% of theory); melting point 185° C. (decomposition). The complex was characterized by means of IR-, $^1$H- and $^{31}$P-NMR- as well as mass spectrum.

Cationic complexes with other 1,2-diphosphines and other supporting ligands can be prepared in a comparable manner.

[Ir (1,5 COD)(RR)-NBDPP]PF$_6$

This complex can be prepared in the same manner by using NH$_4$PF$_6$ instead of NaBF$_4$. Melting point 215° C. (decomposition).

[Ir(1.5 COD)((R.R)-BDPPP)]BF$_4$ 1.03 g [Ir(1,5-COD)Cl]$_2$ (1.53 mmoles) and 1.34 g (R.R)-3,4-bis(diphenylphosphino)-pyrrolidine (=BDPPP) (3.9 mmoles) are dissolved under argon at 0° C. in 70 ml absolute methanol. The reddish violet solution which forms is immediately combined with 0.6 g NaBF$_4$ (5.46 mmoles), dissolved in 90 ml water (free of O$_2$). A flocculent, grayish red precipitate forms which is filtered off after a further hour of agitation and is discarded. In order to precipitate the product, the reddish violet mother liquor is now compounded at 0° C. with 100 ml water (free of O$_2$). Then, a separation via a frit is carried out. The residue is washed with 15 ml water (free of O$_2$). After drying, a recrystallization from methylene chloride/ether is carried out, yielding a dark red powder which melts at 218° C. under decomposition and which was characterized as the specified complex, based on spectroscopic tests.

d) Preparation of Neutral Ir Complexes: [Ir(1,5-COD)((R.R)-NBDPP)Cl]

2.4 g [Ir(1,5-COD)Cl]$_2$ (3.57 mmoles) are placed with 3.97 g (R.R)-NBDPP (7.5 mmoles) in a Schlenk tube, evacuated and combined under argon with 50 ml absolute ethanol. The pale red solution is agitated 2 h at room temperature, during which time a beige precipitate forms which is separated via a frit. Three washes with 10 ml absolute ether per wash are performed and the substance is dried in a high vacuum. A recrystallization is carried out as needed from methylene chloride/ether. Melting point 195° C.; yield 87.3%. The complex was characterized by IR-, NMR- and mass spectra.

EXAMPLE 4

Asymmetric hydrogenations of ketopantolactone with cationic Ir complexes and succinimide as co-catalysts. The conditions of hydrogenation and the results are given in Table 3; the hydrogenation temperature was 50° C.

See Table 3

EXAMPLE 5

The asymmetric hydrogenation of ketopantolactone with neutral Ir complexes and succinimide as co-catalyst. The conditions of hydrogenation and the results are given in Table 4; the hydrogenation temperature was 50° C.

See Table 4

EXAMPLE 6

The asymmetric hydrogenation of ketopantolactone with [Ir(COD)Cl]$_2$/diphosphine of the type of general Formula Ic and succinimide as co-catalyst. Conditions of hydrogenation: Pressure=1.0 MPa; temperature=50° C.; time=6 hours; (S)/(K)=200; solvent-=toluene/tert. butanol (1:3); (CK)/(K) [This is the molar ratio of co-catalyst to catalyst.]=1:10; for the diphosphine added and results, see Table 5.

TABLE 3

| Example | Catalyst | Solvent | (S)/(K) | (CK)/(K) | Pressure (MPa) | Time (h) | Conversion (%) | Enantiomeric excess (% ee (R)) |
|---------|----------|---------|---------|----------|----------------|----------|----------------|-------------------------------|
| 4.1 | [Ir(COD)((RR)-NBDPP]BF$_4$ | Toluene | 203 | 10 | 1.0 | 9 | 38.2 | 84.4 |
| 4.2 | as 4.1 | Toluene/tert. butanol (1:3) | 207 | 10 | 1.0 | 1.5 | 100 | 88.8 |
| 4.3 | as 4.1 | Toluene/tert. butanol (1:3) | 1102 | 10 | 10.8 | 24 | 100 | 84.6 |

TABLE 3-continued

| Example | Catalyst | Solvent | (S)/(K) | (CK)/(K) | Pressure (MPa) | Time (h) | Conversion (%) | Enantiomeric excess (% ee (R)) |
|---|---|---|---|---|---|---|---|---|
| 4.4 | [Ir(COD)((R,R)-BDPPP)]BF₄ | Toluene | 226 | 10 | 0.5 | 23 | 28.4 | 83.6 |
| 4.5 | as 4.4 | Toluene/methanol (1:3) | 228 | 10 | 0.5 | 9 | 99.2 | 65.0 |
| 4.6 | as 4.1 | Methanol | 200 | 5 | 0.5 | 9 | 45.8 | 54.8 |
| 4.7 | as 4.1 | Toluene/methanol (1:1) | 200 | 5 | 0.5 | 9 | 100 | 70.9 |

(S)/(K) = molar ratio of substrate:catalyst
(CK)/(K) = molar ratio of co-catalyst:catalyst
See example 3 for abbreviations of the catalysts

TABLE 4

| Example | Catalyst | Solvent | (S)/(K) | (CK)/(K) | Pressure (MPa) | Time (h) | Conversion (%) | Enantiomeric excess (% ee (R)) |
|---|---|---|---|---|---|---|---|---|
| 5.1 | [Ir(COD)Cl]₂ 2(R,R)-NBDPP (in situ) | Toluene/tert-butanol (1:3) | 209 | 10 | 1.0 | 2.5 | 100 | 88.8 |
| 5.2 | as 5.1 | as 5.1 | 1028 | 10 | 11.0 | 2.0 | 100 | 85.6 |
| 5.3 | [Ir(COD)((R,R)-NBDPP)Cl] (Isolated) | as 5.1 | 210 | 10 | 0.5 | 2.5 | 100 | 89.5 |
| 5.4 | as 5.3 | as 5.1 | 1064 | 10 | 10.6 | 4.0 | 100 | 82.0 |
| 5.5 | [Ir(COD)Cl]₂ 2(R,R)-BDPPP (in situ) | as 5.1 | 215 | 10 | 1.0 | 2.5 | 100 | 79.0 |
| 5.6 | as 5.5 | as 5.1 | 1014 | 10 | 10.9 | 5.0 | 100 | 84.0 |
| 5.7 | [Ir(COD)Cl]₂ 2(R,R)-Norphos (in situ) | as 5.1 | 205 | 10 | 1.0 | 7.0 | 100 | 89.2 |
| 5.8 | as 5.7 | as 5.1 | 1033 | 10 | 11.1 | 3.0 | 100 | 88.8 |
| 5.9 | as 5.1 | Toluene/CH₃OH (1:3) | 500 | 10 | 0.5 | 9.0 | 58.7 | 7.8 |
| 5.10 | as 5.1 | Toluene/n-butanol (1:3) | 500 | 10 | 0.5 | 9.0 | 10.2 | 57.2 |
| 5.11 | as 5.1 | Toluene/i-butanol (1:3) | 500 | 10 | 0.5 | 9.0 | 46.2 | 70.0 |
| 5.12 | as 5.1 | Toluene/tert-butanol (1:3) | 500 | 10 | 0.5 | 9.0 | 100 | 86.4 |

TABLE 5

| Example | Opt. active diphosphane (type I c) | Conversion (%) | Enantiomeric excess (% ee) | (configuration) |
|---|---|---|---|---|
| 6.1 | (2S,3S)-2,3-bis(diphenylphosphino)-butane | 29.7 | 37.4 | (S) |
| 6.2 | (R)-1,2-bis(diphenylphosphino)-3-methylbutane | 45.0 | 23.6 | (R) |
| 6.3 | (R)-1,2-bis(diphenylphosphino)-propane | 41.7 | 30.6 | (R) |

EXAMPLE 7

TABLE 6

| Co-catalyst | Conversion | Enantiomeric excess (% ee) | (configuration) |
|---|---|---|---|
| Succinimide | 100 | 80.4 | (R) |
| Phthalimide | 97 | 58.8 | (R) |
| Glutarimide | 64.3 | 8.2 | (S) |

Pyruvic acid ethyl ester was hydrogenated in a manner analogous to Example 5 using the catalyst [Ir(COD)Cl]₂/2 NBDPP prepared in situ and succinimide as co-catalyst for 23 hours at 50° C. The operating conditions and results are given in Table 7.

TABLE 7

| Example | Solvent | (S)/(K) | (CK)/(K) | Pressure (MPa) | Yield (%) | Enantiomeric excess (% ee (R)) |
|---|---|---|---|---|---|---|
| 8.1 | Toluene | 203 | Without CK | 5.4 | 50 | 5.6 |
| 8.2 | Toluene | 203 | 1.0 | 5.5 | 55 | 10.8 |
| 8.3 | Toluene/tert. butanol | 198 | 10.0 | 10.8 | 99 | 10.4 |

(CK)/(K) = molar ratio of co-catalyst:catalyst

Ketopantolactone was hydrogenated to pantolactone using the catalyst [Ir(COD)Cl]₂/2 NBDPP and a co-catalyst: Hydrogenation temperature=50° C.; pressure=5.3 MPa; time=6 hours; solvent=toluene/tert. butanol (1:3); substrate: catalyst (molar ratio) 500:1; co-catalyst: catalyst (molar ratio) 10:1. Co-catalyst and results see Table 6.

What is claimed is:

1. A method for the asymmetric hydrogenation of α-ketocarbonyl compounds selected from the group consisting of α-ketocarboxylic acid esters, and α-ketolactones to the corresponding optically active α-hydroxycarbonyl compounds in the presence of chiral platinum-metal diphosphine complexes as catalyst;

the improvement wherein the chiral platinum group-metal complexes are chiral iridium complexes which contain an optically active 1,2-diphosphine ligand of the general Formula Ia, Ib or Ic,

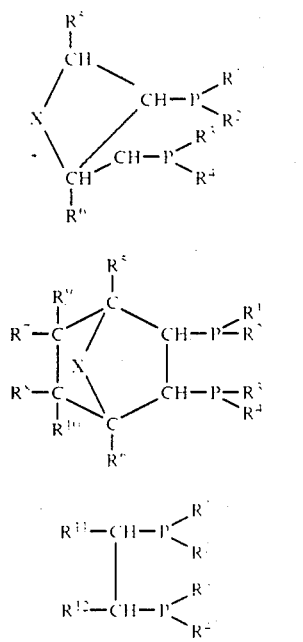

in which
R$^1$, R$^2$, R$^3$ and R$^4$ are the same or different and signify C$_1$ to C$_8$ alkyl, which can be linear or branched, a cyclohexylmethyl, C$_5$ to C$_7$ cycloalkyl, which can have one or two C$_1$ to C$_4$ alkyl substituents, benzyl or phenyl, the aromatic ring of which can contain C$_1$ to C$_4$ alkyl-, C$_1$ to C$_4$ alkoxy-, di-(C$_1$ to C$_4$) alkylamino- or C$_1$ to C$_4$ alkyloxycarbonyl substituents or R$^1$R$^2$ and/or R$^3$R$^4$ represent an orthobiphenylene group, X stands for oxygen, the group NR$^{13}$, CR$^{14}$R$^{15}$, -CR$^{14}$=CR$^{15}$- or -CHR$^{14}$-CHR$^{15}$-, in which R$^{13}$ signifies hydrogen, C$_1$ to C$_6$ alkyl, C$_5$ to C$_7$ cycloalkyl, benzyl or an acyl group from the series -COalkyl, -COaryl, -COOalkyl, -COOaryl, -SO$_2$aryl, -P(O)aryl$_2$, in which the alkyl group contains 1 to 4 carbon atoms and aryl stands for phenyl or naphthyl and can contain one or two C$_1$ to C$_4$ alkyl-, C$_1$ to C$_4$ alkoxy-, di-(C$_1$ to C$_4$) alkylamino-, C$_1$ to C$_4$ alkoxycarbonyl substituents and R$^{14}$ and R$^{15}$ are the same or different and signify hydrogen, C$_1$ to C$_4$ alkyl or phenyl, R$^5$ and R$^6$ are the same or different and signify hydrogen, C$_1$ to C$_4$ alkyl or phenyl, R$^7$ and R$^8$ are the same or different and signify hydrogen, phenyl, C$_1$ to C$_4$ alkoxycarbonyl or C$_1$ to C$_4$ alkyl, R$^9$ and R$^{10}$ constitute a double bond in common or signify hydrogen, R$^{11}$ and R$^{12}$ are the same or different and signify C$_1$ to C$_6$ alkyl, benzyl or phenyl, one of the groups R$^{11}$ and R$^{12}$ can also be hydrogen or, under the condition that at least one phosphorus atom or one of the groups R$^1$ to R$^4$ is chiral, R$^{11}$ and R$^{12}$ also stand for hydrogen.

and wherein the hydrogenation is carried out in the presence of a co-catalyst from the group of cyclic dicarboxylic acid imides of the general Formula II

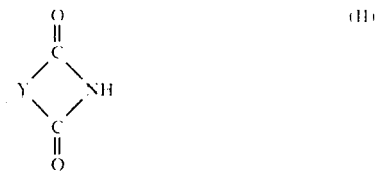

in which Y signifies an ethylene- or tri- or tetra-methylene group, which may be substitute with a phenyl group or one or two C$_1$ to C$_8$ alkyl substituents, or Y is a vinylene- or ortho-arylene group, which can contain one or two substituents from the group (C$_1$ to C$_4$) alkyl, (C$_1$ to C$_4$) alkoxy, (C$_1$ to C$_4$) alkoxycarbonyl, di-(C$_1$ to C$_4$) alkylamino.

2. A method as set forth in claim 1 in which an iridium complexes of the general Formula IIIa or IIIb

[Ir(en)$_2$ (1,2-DP)] A   (IIIa)

[Ir(Z) (en)$_2$ (1,2 DP)]   (IIIb)

is used as catalyst, in which 1,2-DP signifies an optically active 1,2-diphosphine ligand of the general Formula Ia, Ib or Ic, (en)$_2$ signifies two molecules of a monoolefin or a molecule of a diolefin, A signifies a non-coordinating anion, and Z signifies a coordinating anion, which can also be present in the form of an ion exchanger.

3. A method as set forth in claim 2 in which A is selected from the group consisting of BF$_4^-$, PF$_6^-$ and ClO$_4^-$.

4. A method as set forth in claim 2 in which Z is chloride or carboxylate.

5. A method as set forth in claim 1 or claim 2 in which 1,2-diphosphine ligands of the general Formula Ia, Ib or Ic are used in which R$^1$=R$^3$ and R$^2$=R$^4$.

6. A method as set forth in claim 5 in which R$^1$, R$^2$, R$^3$ and R$^4$ are phenyl groups.

7. A method as set forth in claim 1 or claim 2 in which 1,2-diphosphine ligands of the general Formula Ia are used in which R$^5$ and R$^6$ signify hydrogen, X is the group NR$^{13}$ and R$^1$=R$^3$ and R$^2$=R$^4$.

8. A method as set forth in claim 7 in which R$^1$, R$^2$, R$^3$ and R$^4$ are the same.

9. A method as set forth in claim 1 or claim 2 in which 1,2-diphosphine ligands of the general Formula Ib are used in which R$^5$, R$^6$, R$^7$ and R$^8$ signify hydrogen, X signifies a methylene group and R$^1$=R$^3$ and R$^2$=R$^4$.

10. A method as set forth in claim 9 in which R$^1$, R$^2$, R$^3$ and R$^4$ are the same.

11. A method as set forth in claim 1 or claim 2 in which 1,2-diphosphine ligands of the general Formula Ic are used in which R$^{11}$ signifies hydrogen or a methyl group and R$^{12}$ signifies a C$_1$ to C$_4$ alkyl group which can be linear or branched.

12. A method as set forth in claim 1 or claim 2 in which succinimide is used as co-catalyst in an amount of 1 to 50 moles, per mole of iridium complex.

13. A method as set forth in claim 12 in which succinimide is used as co-catalyst in a amount of 2 to 25 moles, per mole of iridium complex.

14. A method as set forth in claim 1 or claim 2 in which ketopantolactone is hydrogenated to (R)-(−)-pantolactone.

15. A method as set forth in claim 1 or claim 2 in which the active catalyst of the general Formula IIIb is first prepared in situ from an Ir complex of the formula [Ir (en)$_2$ (Z)]$_2$, in which (en)$_2$ signifies two molecules of a monoolefin or a molecule of a diolefin and Z signifies a coordinating anion, which can also be present in the form of an ion exchanger, by means of the addition of the optically active 1,2-diphosphine of Formula Ia, Ib or Ic in at least one solvent used for the hydrogenation, and the ketocarbonyl compound is hydrogenated in the presence of the catalytic solution obtained in this manner.

16. A method as set forth in claim 1 or claim 2 in which the ketocarbonyl compound and the Ir complex are used in a molar ratio of 200 to 2000, and the hydrogenation is carried out at a pressure of 0.1 to 20 MPa and at a temperature of 10° to 100° C.

17. A method as set forth in claim 16 in which the pressure is 0.5 to 12 MPa.

18. A method as set forth in claim 1 or claim 2 in which the hydrogenation is carried out in the presence of a solvent mixture consisting of an aromatic hydrocarbon and a branched or unbranched lower alcohol 19. A method as set forth in claim 18 in which the solvent consists of a mixture of toluene or xylene and a monovalent $C_3$ to $C_5$ alcohol.

20. A method as set forth in claim 19 in which the alcohol is tert. butanol.

* * * * *